(12) United States Patent
Soares et al.

(10) Patent No.: US 10,753,834 B2
(45) Date of Patent: Aug. 25, 2020

(54) FLEX PLATE WITH REMOVABLE INSERTS AND COVER

(71) Applicant: Brookhaven Science Associates, LLC, Upton, NY (US)

(72) Inventors: Alexei Soares, Shirley, NY (US); Karan Joshi, Eatontown, NJ (US); Lauren E. Zipper, Miller Place, NY (US); Grace Shea-McCarthy, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 374 days.

(21) Appl. No.: 15/541,782

(22) PCT Filed: Jan. 8, 2016

(86) PCT No.: PCT/US2016/012567
§ 371 (c)(1),
(2) Date: Jul. 6, 2017

(87) PCT Pub. No.: WO2016/112239
PCT Pub. Date: Jul. 14, 2016

(65) Prior Publication Data
US 2018/0003599 A1    Jan. 4, 2018

Related U.S. Application Data

(60) Provisional application No. 62/100,962, filed on Jan. 8, 2015.

(51) Int. Cl.
| | |
|---|---|
| *G01N 1/28* | (2006.01) |
| *C30B 7/14* | (2006.01) |
| *C30B 29/58* | (2006.01) |
| *C07K 1/30* | (2006.01) |
| *G01N 23/207* | (2018.01) |
| *C07H 21/00* | (2006.01) |

(52) U.S. Cl.
CPC ........... *G01N 1/2806* (2013.01); *C07K 1/306* (2013.01); *C30B 7/14* (2013.01); *C30B 29/58* (2013.01); *G01N 23/2076* (2013.01); *C07H 21/00* (2013.01); *G01N 2223/307* (2013.01)

(58) Field of Classification Search
CPC ...... G01N 1/28; G01N 23/2076; C07K 1/306; C30B 7/14; C30B 29/58; C07H 21/00
USPC ......................................................... 23/300
See application file for complete search history.

(56) References Cited

U.S. PATENT DOCUMENTS

| | | |
|---|---|---|
| 2009/0155145 A1 | 6/2009 | Viola et al. |
| 2009/0264632 A1 | 10/2009 | Sommer |

FOREIGN PATENT DOCUMENTS

WO    2013148938 A1    10/2013

OTHER PUBLICATIONS

International Search Report and Written Opinion, PCT/US2016/012567 (dated Mar. 31, 2016), 14pp.
Dunlop, K. V., et al., "A modified vapor-diffusion crystallization protocol that uses a common dehydrating agent", Acta Cryst., D61, Biological Crystallography, International Union of Crystallography, pp. 1041-1048 (2005).

*Primary Examiner* — Edward M Johnson
(74) *Attorney, Agent, or Firm* — Dorene Price

(57) ABSTRACT

Technologies are described for methods and systems effective for flex plates. The flex plates may comprise a base plate. The base plate may include walls that define an insert location opening in the base plate. The insert location opening in the base plate may be in communication with a securement area. The flex plates may comprise an insert. The insert may include a reservoir region and a crystallization region separated by a wall including channels. The reservoir region and the crystallization region may include a backing. The insert may further include securement tabs. The securement tabs may be configured to secure the insert to the base plate at the securement area.

14 Claims, 4 Drawing Sheets

US 10,753,834 B2

FLEX PLATE WITH REMOVABLE INSERTS AND COVER

This application claims benefit of U.S. Provisional Application No. 62/100,962 filed on Jan. 8, 2015, the contents of which are incorporated herein by reference in its entirety.

The present application was made with government support under contract number DE-SC0012704 awarded by the U.S. Department of Energy. The United States government has certain rights in the invention(s).

FIELD OF THE INVENTION

This disclosure relates generally to a tray for growing crystals such as proteins, nucleic acids, and/or carbohydrates. Crystals grown in crystallization trays may be analyzed for applications involving drug design and for controlling drug delivery.

BACKGROUND

Molecules such as proteins, nucleic acids, and/or carbohydrates may be crystallized in order to study the crystalline structure to obtain detail about the molecules' function. Crystallization may be performed by providing a preparation of a solution of a target compound and altering the environment of the dissolved target compound to make the target compound revert to its solid form as a crystal. A precipitate may be introduced into the environment to make the target compound less soluble and to induce crystallization.

SUMMARY

In some examples, flex plates are generally described. The flex plates may comprise a base plate. The base plate may include walls that define an insert location opening in the base plate. The insert location opening in the base plate may be in communication with a securement area. The flex plates may comprise an insert. The insert may include a reservoir region and a crystallization region separated by a wall including channels. The reservoir region and the crystallization region may include a backing. The insert may further include securement tabs. The securement tabs may be configured to secure the insert to the base plate at the securement area.

In some examples, methods to make samples are generally described. The methods may comprise placing a preparation within a crystallization region of an insert secured to a base plate. The methods may comprise placing a precipitant within a reservoir region of the insert. The reservoir region may be separated from the crystallization region by walls defining channels. The methods may comprise allowing vapor from the precipitant to achieve equilibrium between the reservoir region and the crystallization region. The methods may comprise removing the insert from the base plate. The methods may comprise placing the insert into a testing device to test the sample.

In some examples, flex plates are generally described. The flex plates may comprise a base plate wherein the base plate includes walls that define an insert location opening in the base plate. The insert location opening may be in communication with a securement area. The flex plates may comprise an insert. The insert may include a reservoir region and a crystallization region separated by a wall including channels. The reservoir region and the crystallization region may include a backing. The insert may further include securement tabs. The securement tabs may be configured to secure the insert to the base plate at the securement area. The flex plates may comprise a cover. The cover may include an adhesive sheet configured to cover the flex plate and define holes. The holes may be configured such that preparation and precipitant may be placed in at least one of the crystallization region and the reservoir region through the cover.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
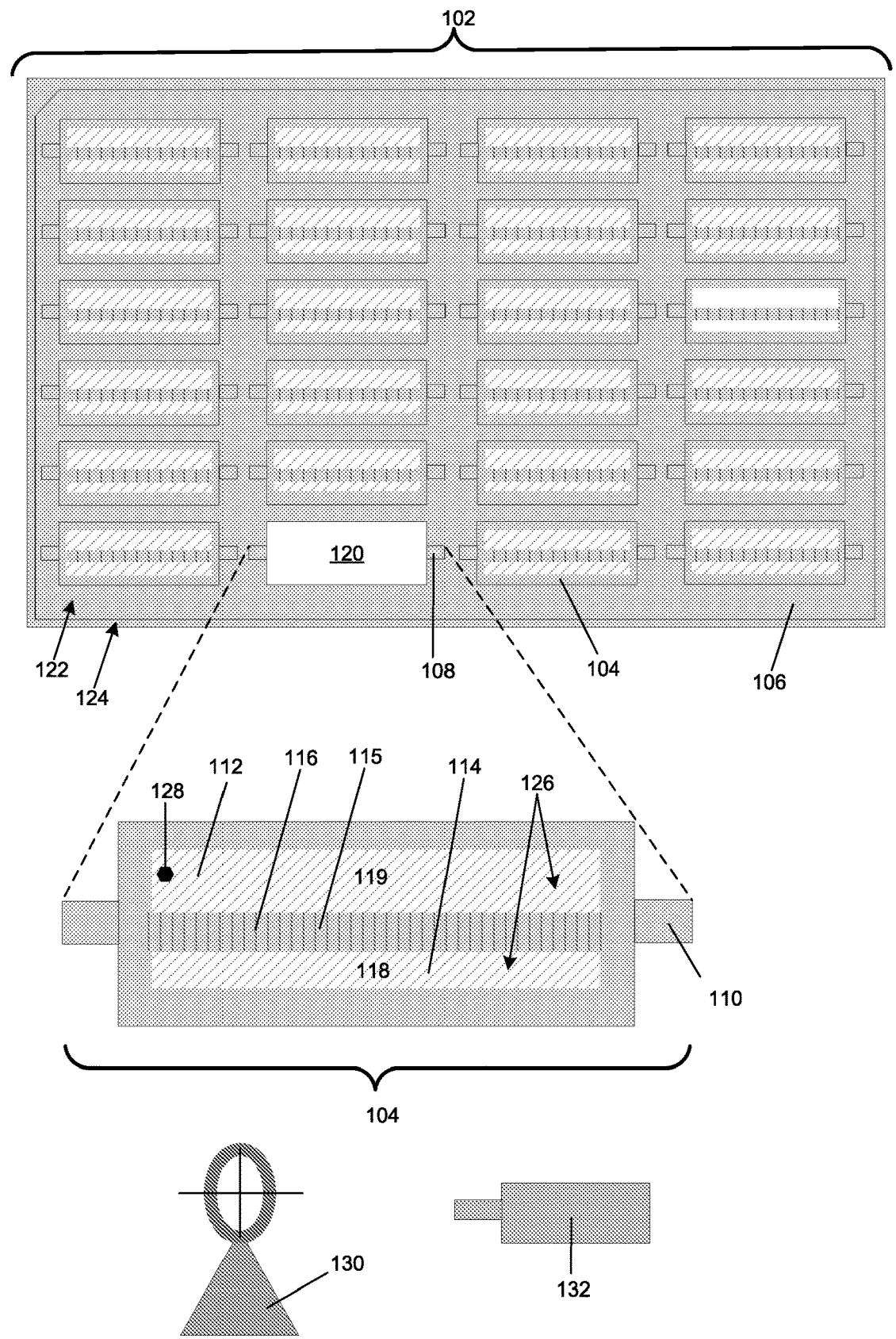
FIG. 1 illustrates an example flex plate with a removable insert removed.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example flex plate with a removable insert removed, arranged in accordance with at least some embodiments presented herein. As discussed in more detail below, a flex plate used for crystal growth may include removable inserts which may be removed from the flex plate and utilized for in situ data collection.

Flex plate 102 may be a crystal growth plate used to grow crystals such as proteins, nucleic acids, and/or carbohydrates. Flex plate 102 may include a base plate 106 and multiple fragments or removable inserts 104. Flex plate 102, including base plate 106, and fragments or removable inserts 104 may be made from a polymer material such as acrylonitrile-butadiene-styrene copolymer, polycarbonate, polydimethylsiloxane (PDMS), polyethylene (PE), polymethylmethacrylate (PMMA), polymethylpentene, polypropylene, polystyrene, polysulfone, polytetrafluoroethylene (PTFE), polyurethane (PU), polyvinylchloride (PVC), polyvinylidene chloride (PVDC), polyvinylidine fluoride, styrene-acryl copolymers, polyisoprene, polybutadiene, polychloroprene, polyisobutylene, poly(styrene-butadiene-styrene), silicones, epoxy resins, poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN), polyamide (PA), polyamide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), and mixtures thereof.

Insert 104 may include securement tabs 110, walls defining a crystallization region 112, walls defining a reservoir region 114, and walls defining channels 116. Insert 104 may include transparent backing 126 that may be adhered to both crystallization region 112 and to reservoir region 114. Transparent backing 126 may be adhered to an underside of insert 104 and may be transparent to electromagnetic radiation such as x-rays. Securement tabs 110 may secure insert 104 to base plate 106 through a mating between securement tabs 110 and a securement area 108 defined by walls in base plate 106. Securement tabs 110 may secure insert 104 to base plate 106 such that insert 104 may be removed or disassembled from base plate 106. Securement of insert 104 to base plate 106 may be performed by any securement method, including, dovetailing, snap-in, friction fit, sockets, etc. Securement tabs 110 may also be compatible with adapters for goniometers.

Base plate 106 may include walls which define insert location openings 120. Insert location openings 120 may communicate with securement area 108. Insert 104 may be secured within insert location openings 120 when securement tabs 110 mate with securement areas 108. Flex plate 102 may include base plate 106 with a respective insert 104 secured within each insert location opening 120. Flex plate 102, including inserts 104 secured in flex plate base 106, may be used to grow protein crystals for protein crystallography. Base plate 106 of flex plate 102 may include a raised area 122 above a pedestal 124. Flex plate 102 may be about 128 mm in length (at longest point on pedestal 124), by about 85.5 mm in width (at widest point on pedestal 124), by about 11.5 mm high (total height of pedestal 124 and raised area 122). Flex plate 102 may be configured to have preparations and precipitants applied to crystallization region 112 and precipitant region 114 respectively, by protein crystallography automated equipment.

Crystallization region 112 of insert 104 may be separated from reservoir region 114 by wall 115. Wall 115 may prevent liquid precipitant 118 from crossing from reservoir region 114 to crystallization region 112. Channels 116 may be defined by wall 115 along a top edge of wall 115. Channels 116 may be grooves within the top edge of wall 115 running between reservoir region 114 and crystallization region 112 and may allow air and vapor of precipitant 118 to flow between reservoir region 114 and crystallization region 112. Crystallization region 112 of each insert 104 may accommodate chemical screening preparations. A liquid handling system, such as acoustic droplet ejection (ADE) may be operated in connection with flex plate 102 and insert 104 to place preparations 119 within crystallization region 112. Crystallization region 112 may accommodate over 81 distinct chemical screening preparations. Reservoir region 114 may include precipitant 118. Precipitant 118 may be any precipitant used in protein crystallography, including but not limited to, poly ethylene glycol (PEG) 600, PEG 4K, PEG 10K, $(NH_4)_2SO_4$, $PO_4$, and citrate. Precipitant 118 in vapor form may diffuse across channels 116 to crystallization region 112. Precipitant 118 in vapor form may achieve equilibrium between reservoir region 114 and crystallization region 112. Precipitant vapor equilibrium may take a time period, such as 24 hours and crystals may form in crystallization region 112. As discussed in more detail below, a cover may be placed over insert 104 or flex plate 102, including multiple inserts, to prevent loss of precipitate when preparation volumes are of nanoliter scale.

Upon formation of crystals 128, or at an end of crystal preparation, if no crystal forms, the flex plate cover may be removed from flex plate 102 and insert 104. Flex plate 102 may be covered with an x-ray transparent adhesive plastic plate cover. The adhesive plastic plate cover may be cut with a razor blade such that each insert 104 is separated from other inserts 104. Each insert 104 may be removed or disassembled from base plate 106. Insert 104 may provide for in situ data collecting, as securement tabs 110 of insert 104 may be placed within standard mounts for a goniometer 130. Goniometer 130 and x-ray source 132 may thus perform x-ray analysis of samples from within crystalline region 112 of insert 104 while samples are within insert 104.

Figure 2:
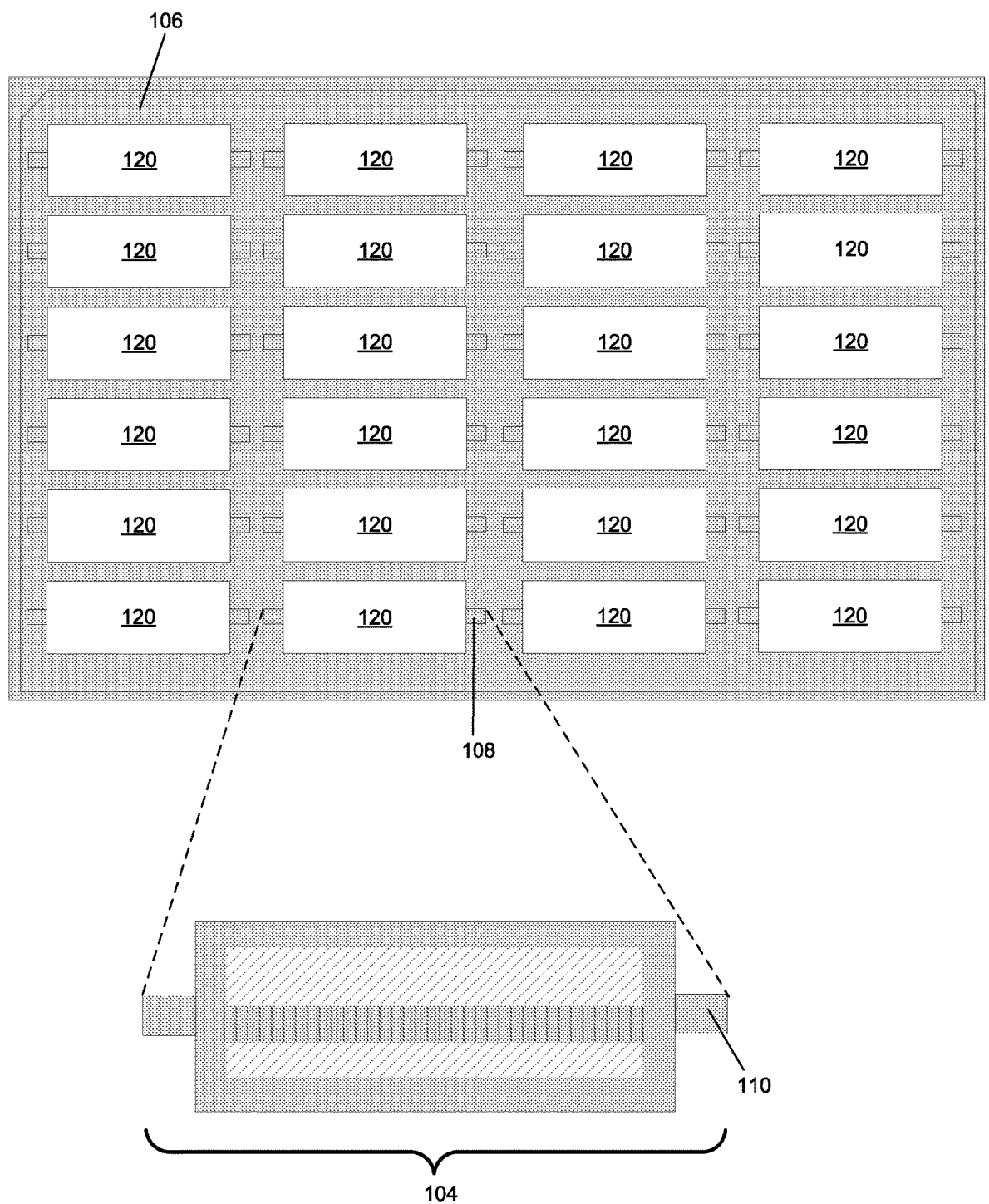
FIG. 2 illustrates an example base plate with a removable insert removed.

FIG. 2 illustrates an example base plate with a removable insert removed, arranged in accordance with at least some embodiments presented herein. Those components in FIG. 2 that are labeled identically to components of FIG. 1 will not be described again for the purposes of clarity.

As previously discussed, base plate 106 may include walls defining insert location openings 120 and securement areas 108. A size of insert 104, as well as location and patterning of inserts 104 within base plate 106 may be varied based on chemical libraries to be used as preparation. In an example, 96 chemicals may be used in 8×12 layouts. Base plates 106 may be configured to accommodate from 1 to 64 inserts 104 in any configuration of 1-16 rows and 1-16 columns, for example, 5 rows by 2 columns, 5 rows by 4 columns, 6 rows by 4 columns, 8 rows by 4 columns, etc.

Figure 3:
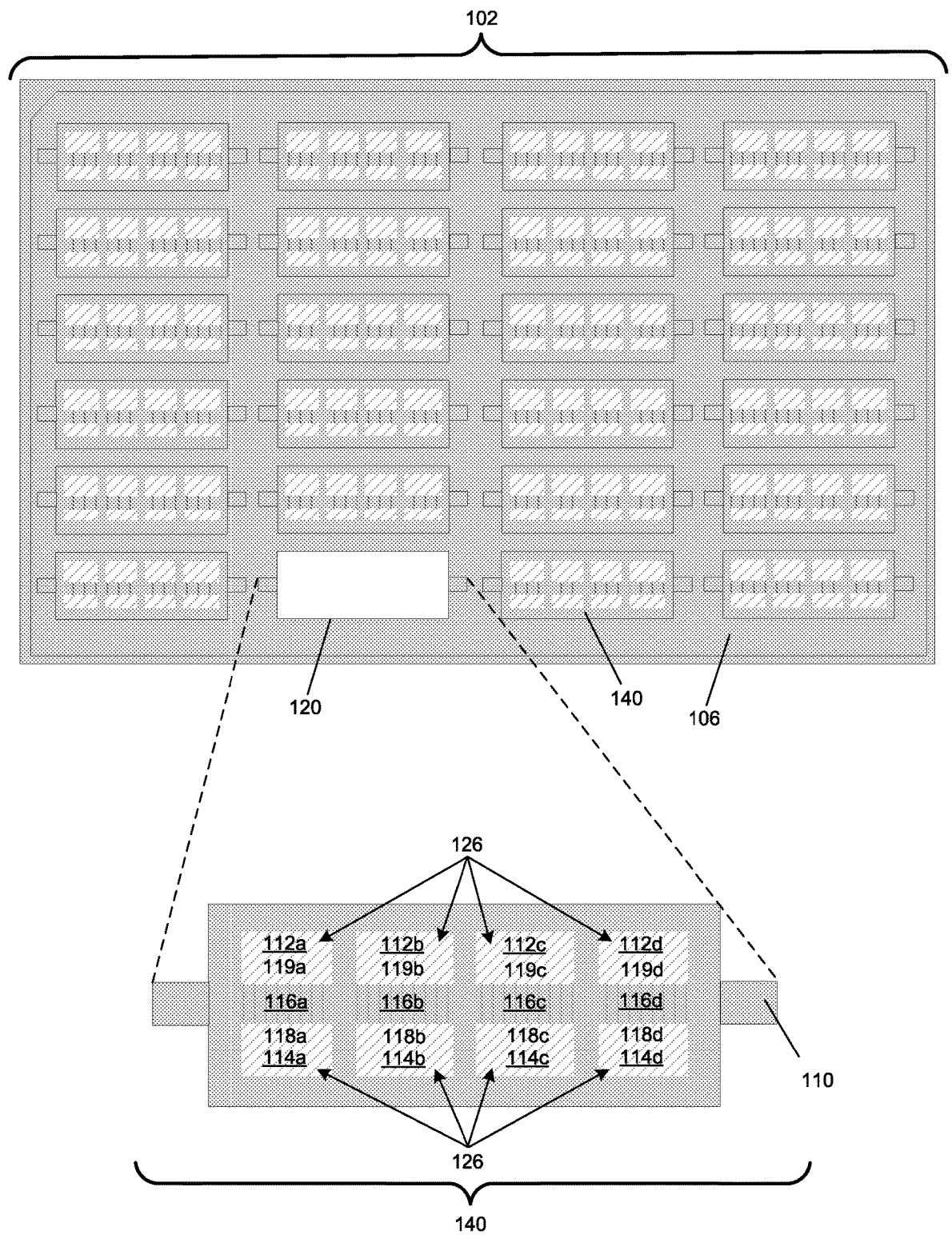
FIG. 3 illustrates an example flex plate including a base plate with removable inserts with multiple reservoir regions and with a removable insert removed.

FIG. 3 illustrates an example flex plate including a base plate with removable inserts with multiple reservoir regions and with a removable insert removed, arranged in accordance with at least some embodiments presented herein. Those components in FIG. 3 that are labeled identically to components of FIGS. 1-2 will not be described again for the purposes of clarity.

Flex plate 102 may include base plate 106 with inserts 140 secured throughout base plate 106 such that an insert 140 is secured within all insert location openings 120 in base plate 106. Flex plate 102 may be prepared with preparations and precipitants in crystallization region 112 and reservoir region 114 by hand or by automated measures such as ADE. As described in more detail below, inserts 140 may be configured for more than one precipitant 118. Flex plate 102 may include insert 140 with different configurations within base plate 106, depending upon the criteria to be tested. For example, an insert 140 configured with one precipitate reservoir may be secured in base plate 106 next to an insert 140 configured with four precipitate reservoirs.

In an example, a protein crystallization experiment may desirably use more than one precipitant 118. Insert 140 may be configured to include more than one reservoir region 114, for example reservoir regions 114*a*, 114*b*, 114*c*, and 114*d*. Precipitants 118*a*, 118*b*, 118*c*, and 118*d* may be prepared and placed in each reservoir region respectively. Precipitants 118*a*, 118*b*, 118*c*, and 118*d*, in vapor form may diffuse across channels 116*a*, 116*b*, 116*c*, and 116*d* to crystallization regions 112*a*, 112*b*, 112*c*, and 112*d* respectively. Crystallization regions 112*a*, 112*b*, 112*c*, and 112*d* may each be prepared with preparations 119*a*, 119*b*, 119*c*, and 119*d* respectively. Preparations 119*a*, 119*b*, 119*c*, and 119*d* may be identical or different preparations. Preparations 119*a*, 119*b*, 119*c*, and 119*d* may grow crystals with precipitants 118*a*, 118*b*, 118*c*, and 118*d* respectively. A configuration of insert 140 may be determined based on preparation criteria and testing to be completed.

Figure 4:
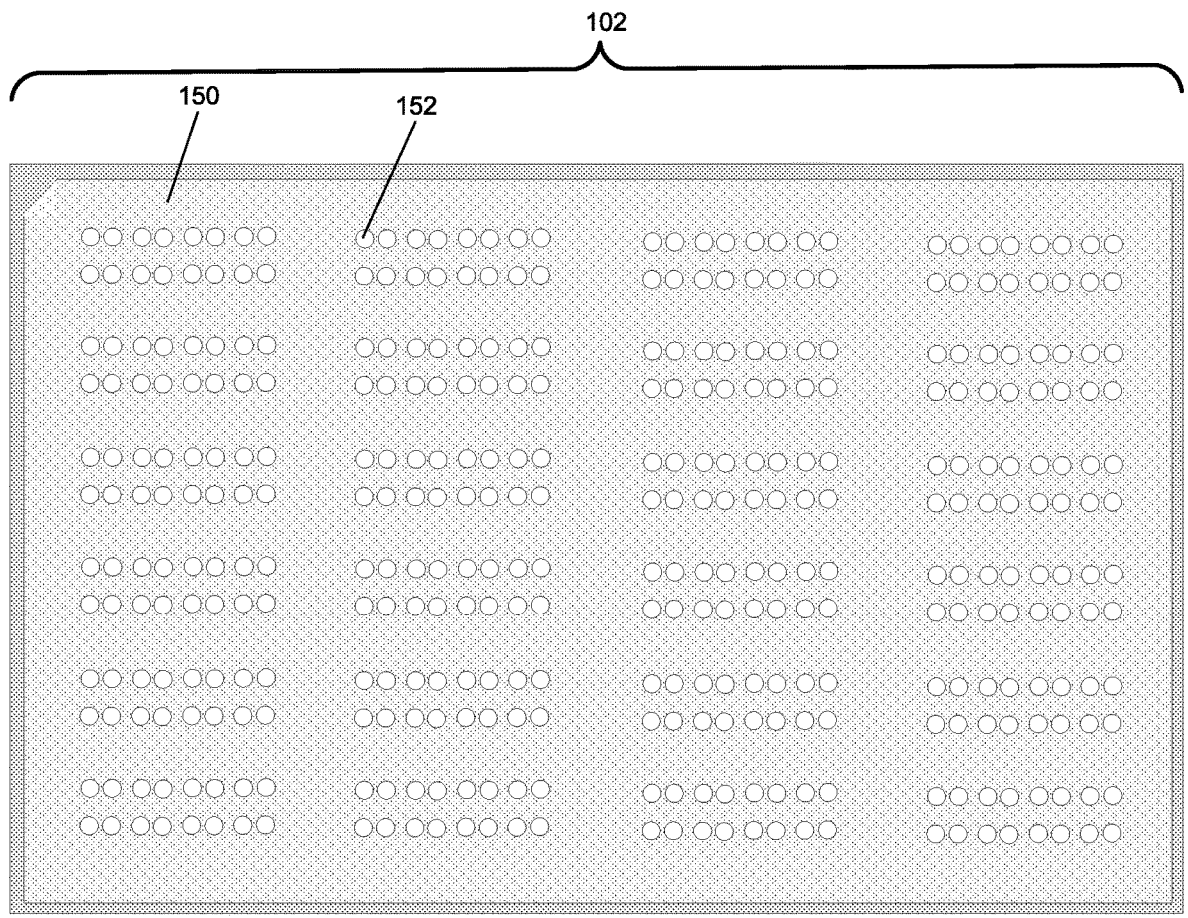
FIG. 4 illustrates an example flex plate cover.

FIG. 4 illustrates an example flex plate cover, arranged in accordance with at least some embodiments herein. Those components in FIG. 4 that are labeled identically to components of FIGS. 1-3 will not be described again for the purposes of clarity.

Flex plate cover 150 may be an adhesive sheet and may cover over the entirety of flex plate 102. Flex plate cover 150 may be transparent. Flex plate cover 150 may define holes 152. Holes 152 may be configured to be located over reservoir regions 114 or crystallization regions 112 of any configuration of flex plate 102 such that preparation 119 and precipitant 118 may be placed within flex plate 102. Flex plate cover 150 may prevent evaporation or loss of vapor precipitant during preparation and growing of crystals when preparation volumes are of nanoliter volumes. Flex plate cover 150 may cover about 96% of flex plate 102. Flex plate cover 150 may be made from a polymer material such as acrylonitrile-butadiene-styrene copolymer, polycarbonate, polydimethylsiloxane (PDMS), polyethylene (PE), polymethylmethacrylate (PMMA), polymethylpentene, polypropylene, polystyrene, polysulfone, polytetrafluoroethylene (PTFE), polyurethane (PU), polyvinylchloride (PVC), polyvinylidene chloride (PVDC), polyvinylidine fluoride, styrene-acryl copolymers polyisoprene, polybutadiene, polychloroprene, polyisobutylene, poly(styrene-butadiene-styrene), silicones, epoxy resins, poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN) polyamide (PA), polyamide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), and mixtures thereof.

Figure 5:
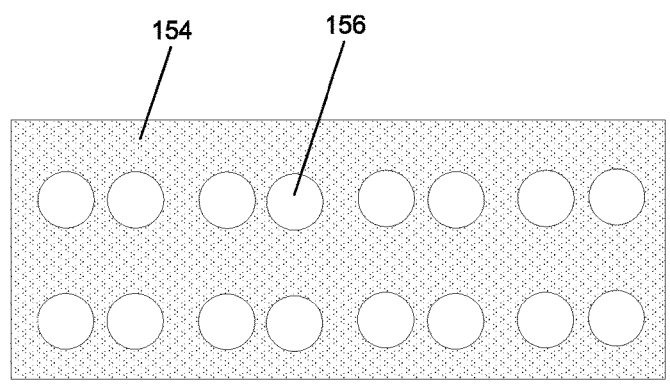
FIG. 5 illustrates an example insert cover; all arranged according to at least some embodiments described herein.

FIG. 5 illustrates an example insert cover, arranged in accordance with at least some embodiments herein. Insert cover 154 may be an adhesive sheet and may cover over the entirety of insert 104. Insert cover 154 may be transparent. Insert cover 154 may define holes 156. Holes 156 may be configured to be located over reservoir regions 114 or crystallization regions 112 of any configuration of insert 104 such that preparation and precipitant may be placed within insert 104. Insert cover 154 may prevent evaporation or loss of vapor precipitant during preparation and growing of crystals within insert 104 when preparation volumes are of nanoliter volumes.

In an example, flex plate 102 may be prepared with an ADE system. A chemical library may be placed by the ADE system at 81 locations in crystallization region 112 of one or more inserts 104 of flex plate 102. Precipitant 118 may be placed in reservoir region 114 of one or more inserts 104 of flex plate 102. Precipitant 118 may be placed with agar or allowed to soak into agar that has hardened in reservoir region 114. Flex plate cover 150 may be placed over the flex plate 102 and equilibrium of precipitant vapor may be reached between reservoir region 114 and crystallization region 112. Flex plate 102 may be placed in a container moistened with precipitant 118 to aid in reaching equilibrium.

Protein and precipitant 118 may be placed by ADE system in crystallization region 112 of one or more inserts 104 through holes 152 in flex plate cover 150. Preparation 119 may include a chemical library, protein and precipitant 118 placed in crystallization region 112. Equilibrium of precipitant 118 vapor may be reached between reservoir region 114 and crystallization region 112. Flex plate 102 may be placed in a container moistened with precipitant 118 to aid in reaching equilibrium. Flex plate 102 may include about 800 or more co-crystallization experiments.

Cover 150 may be removed from flex plate 102. Flex plate 102 may be covered with an x-ray transparent adhesive plastic plate cover. The adhesive plastic plate cover may be cut with a razor blade around each insert such that each insert 104 is separated from other inserts 104. Inserts 104 may then be removed individually from base plate 106. Each insert 104 may be placed onto a magnetic cap and x-ray data may be obtained with a goniometer.

In another example preparation 119 may include first growing a protein sample and then adding a chemical from a chemical library. In addition to a protein sample, precipitant, and a chemical from a chemical library, preparation 119 may also include a chemical additive or other precisely targeted substance ("magic bullet") which may improve diffraction, a cryo protectant, or may include a heavy atom additive.

Among other possible benefits, a system in accordance with the present disclosure may provide for in situ data collecting. Inserts may be removed from a flex plate and the inserts may be placed within standard mounts for a goniometer. The goniometer may thus perform x-ray analysis of crystals formed within the insert while crystals are still within the insert. A user may not have to endure the laborious activity of gathering crystals in order to analyze the crystals with a goniometer. A user may not have to purchase and operate complicated and unreliable robotics to analyze crystals formed in flex plates that may not have removable inserts. A system in accordance with the present disclosure may provide high throughput by eliminating sample collection steps. The inserts may be directly placed into a goniometer as the inserts may be compatible with the centimeter sized throw of x-ray beams. Small amounts of preparations and precipitants may be used as the inserts may be used with nanoliter volumes. Waste may be reduced as the base plates may be reused.

While various aspects and embodiments have been disclosed herein, other aspects and embodiments will be apparent to those skilled in the art. The various aspects and embodiments disclosed herein are for purposes of illustra-

The invention claimed is:

1. A flex plate comprising:
   a base plate, wherein the base plate includes at least one securement area; and
   at least one removable insert in the at least one securement area, wherein the removable insert includes a reservoir region and a crystallization region separated by a wall including channels and the crystallization region has more than one preparations, the reservoir region and the crystallization region include a backing, the removable insert further includes securement tabs, wherein the securement tabs are configured to secure the removable insert to the base plate at the securement area.

2. The flex plate of claim 1, wherein the securement tabs are configured to secure the removable insert to the base plate with one of a dovetail, snap, or socket arrangement.

3. The flex plate of claim 1, wherein the base plate and the removable insert include a polymer material.

4. The flex plate of claim 3, wherein the polymer material is one of acrylonitrile-butadiene-styrene copolymer, polycarbonate, polydimethylsiloxane (PDMS), polyethylene (PE), polymethylmethacrylate (PMMA), polymethylpentene, polypropylene, polystyrene, polysulfone, polytetrafluoroethylene (PTFE), polyurethane (PU), polyvinylchloride (PVC), polyvinylidene chloride (PVDC), polyvinylidine fluoride, styrene-acryl copolymers, polyisoprene, polybutadiene, polychloroprene, polyisobutylene, poly(styrene-butadiene-styrene), silicones, epoxy resins, poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN), polyamide (PA), polyamide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), or mixtures thereof.

5. The flex plate of claim 1, further comprising the base plate including walls that define an insert location opening in the base plate in communication with the at least one securement area, wherein the insert location opening is a first opening and the securement area is a first securement area and the base plate further includes walls defining a second opening and a second securement area.

6. The flex plate of claim 1, wherein the base plate includes walls defining twenty-four openings and securement areas configured six rows by four columns.

7. The flex plate of claim 1, wherein the base plate includes walls defining thirty-two openings and securement areas configured eight rows by four columns.

8. The flex plate of claim 1, further comprising a cover, wherein the cover includes an adhesive configured to cover the flex plate and define holes, the holes being configured such that preparation and precipitant may be placed in at least one of the crystallization region and the reservoir region through the cover.

9. The flex plate of claim 1, wherein the reservoir region is a first reservoir region and the crystallization region is a first crystallization region, and the removable insert further includes a second reservoir region and a second crystallization region.

10. A flex plate comprising:
    a base plate wherein the base plate includes at least one securement area; and
    at least one removable insert in the at least one securement area, wherein the removable insert includes a reservoir region and a crystallization region separated by a wall including channels and the crystallization region having more than one preparations, the reservoir region and the crystallization region include a backing, the removable insert further includes securement tabs, wherein the securement tabs are configured to secure the removable insert to the base plate at the securement area; and
    a cover, wherein the cover includes an adhesive sheet configured to cover the flex plate and define holes, the holes being configured such that more than one preparations and precipitant may be placed in the crystallization region and the reservoir region through the cover.

11. The flex plate of claim 10, wherein the base plate and the removable insert are a polymer material.

12. The flex plate of claim 10, further comprising: more than one preparations in the crystallization region, wherein preparation includes a chemical and a protein; and
    precipitant in the reservoir region.

13. The flex plate of claim 10, further comprising the base plate including walls that define an insert location opening in the base plate in communication with the at least one securement area, wherein the insert location opening is a first opening and the securement area is a first securement area and the base plate further includes walls defining a second opening and a second securement area.

14. The flex plate of claim 10, wherein the cover is one of acrylonitrilebutadiene-styrene copolymer, polycarbonate, polydimethylsiloxane (PDMS), polyethylene (PE), polymethylmethacrylate (PMMA), polymethylpentene, polypropylene, polystyrene, polysulfone, polytetrafluoroethylene (PTFE), polyurethane (PU), polyvinylchloride (PVC), polyvinylidene chloride (PVDC), polyvinylidine fluoride, styrene-acryl copolymers polyisoprene, polybutadiene, polychloroprene, polyisobutylene, poly(styrene-butadiene-styrene), silicones, epoxy resins, poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN), polyamide (PA), polyamide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), or mixtures thereof.

* * * * *